US008265752B2

(12) United States Patent
Armoundas (10) Patent No.: US 8,265,752 B2
(45) Date of Patent: Sep. 11, 2012

(54) SYSTEM AND METHOD FOR ASSESSING ATRIAL ELECTRICAL STABILITY

(75) Inventor: Antonis A. Armoundas, Lincoln, MA (US)

(73) Assignee: The General Hospital Corporation, Boston, MA (US)

(*) Notice: Subject to any disclaimer, the term of this patent is extended or adjusted under 35 U.S.C. 154(b) by 785 days.

(21) Appl. No.: 12/431,558

(22) Filed: Apr. 28, 2009

(65) Prior Publication Data
US 2010/0042172 A1 Feb. 18, 2010

Related U.S. Application Data

(60) Provisional application No. 61/125,691, filed on Apr. 28, 2008, provisional application No. 61/134,325, filed on Jul. 9, 2008.

(51) Int. Cl.
*A61N 1/365* (2006.01)

(52) U.S. Cl. ........... 607/17; 607/14; 607/23; 607/9; 600/500; 600/509

(58) Field of Classification Search ........... 607/23, 607/17; 600/500, 509
See application file for complete search history.

(56) References Cited

U.S. PATENT DOCUMENTS

| | | | |
|---|---|---|---|
| 5,626,623 A * | 5/1997 | Kieval et al. | ........ 607/23 |
| 6,453,191 B2 | 9/2002 | Krishnamachari | |
| 6,735,466 B1 | 5/2004 | Haghighi-Mood | |
| 6,915,156 B2 | 7/2005 | Christini et al. | |
| 7,162,299 B1 * | 1/2007 | Kroll et al. | ........ 607/14 |
| 7,502,643 B2 * | 3/2009 | Farringdon et al. | ........ 600/509 |
| 7,756,571 B1 | 7/2010 | Farazi | |
| 8,005,533 B1 | 8/2011 | Farazi | |

FOREIGN PATENT DOCUMENTS

| | | |
|---|---|---|
| WO | 2007013911 | 2/2007 |
| WO | 2009048845 | 4/2009 |

OTHER PUBLICATIONS

Soria, M Llamedo et al.; "A Multilead Wavelet-based ECG Delineator Based on the RMS Signal; " Computers in Cardiology 2006; 33:153-156.

Krogh-Madsen, Trine; Christini, David J.; "Action Potential Duration Dispersion and Alternans in Simulated Heterogeneous Cardiac Tissue with a Structural Barrier;" Biophysical Journal, vol. 92 Feb. 2007; 1138-1149.

* cited by examiner

*Primary Examiner* — Carl H. Layno
*Assistant Examiner* — Jon-Eric C. Morales
(74) *Attorney, Agent, or Firm* — Quarles & Brady LLP (57) ABSTRACT

A method for identifying a susceptibility of a subject to atrial-rhythm disturbances includes a) placing a plurality of sensors on the subject to measure a physiologic signal of the subject, and b) recording the physiologic signal from the sensor. The physiologic signal includes an atrial electrical activity of the subject. The method includes c) determining a beat-to-beat variability in the atrial electrical activity of the subject. The beat-to-beat variability includes alternans of electrocardiographic waveforms of a predetermined number of a sequence of heart beats. The method includes d) determining a susceptibility to atrial-rhythm disturbances of the subject using the beat-to-beat variability in the atrial electrical activity determined in step c), and e) generating a report of the susceptibility to atrial-rhythm disturbances of the subject.

21 Claims, 8 Drawing Sheets

FIG. 9

SYSTEM AND METHOD FOR ASSESSING ATRIAL ELECTRICAL STABILITY

CROSS-REFERENCE TO RELATED APPLICATIONS

This application is based on, claims the benefit of, and incorporates by reference U.S. Provisional Application Ser. No. 61/125,691 filed Apr. 28, 2008, and entitled "Method and Apparatus for Assessing Atrial Electrical Stability" and U.S. Provisional Application Ser. No. 61/134,325 filed Jul. 9, 2008, and entitled "Method and Apparatus for Assessing Atrial Electrical Stability."

BACKGROUND

Cardiovascular disease is the greatest cause of morbidity and mortality in the industrialized world. It not only strikes down a significant fraction of the population without warning but also causes prolonged suffering and disability in an even larger number.

Atrial fibrillation (AF) is a common arrhythmia, affecting approximately 1% of the general population and 8% of those over the age of 80. As a result, AF places a substantial financial burden on the healthcare system, accounting for over $6 billion in direct treatment costs in the United States in 2006. More importantly, AF is associated with substantial morbidity and mortality. For example, several studies have documented a two-fold increase in mortality and a 2 to 7-fold increase in stroke rate for patients in AF compared to age-matched controls in normal sinus rhythm. Unfortunately, current pharmacologic therapy for the prevention of AF (anti-arrhythmic drugs) is hampered by major dose-limiting toxicities and high rates of arrhythmia recurrence.

In some cases, radio-frequency catheter ablation of the pulmonary veins is used to isolate unorganized electrical activity generated therein to prevent AF. Current catheter based techniques generally use an anatomic approach to identify ablation targets—regions targeted for radio-frequency ablation are identified largely based on their anatomic proximity to the pulmonary veins resulting in the same basic set of ablation lesions being generated in all patients. Using this approach, however, long-term success has been limited with an AF recurrence rate of up to 50% within 12 months following a single ablation procedure. The limited efficacy of pulmonary vein ablation is at least partly due to the fact that atrial fibrillation is a heterogeneous disease and arises from different sites in different patients.

In fact, many non-pulmonary vein sites have been identified as potential triggers for AF. Unfortunately, methods to identify these other sites during ablation procedures are lacking. In addition to the pulmonary veins, other cardiac veins are potentially arrhythmogenic, and may also be involved in the initiation and perpetuation of AF.

More recent techniques for AF ablation have used complex electroanatomic mapping systems to identify non-pulmonary vein sites as targets for ablation. These newer methods are technically complex, difficult to apply broadly and still do not provide an easily applied measure for defining the adequacy of ablation.

Pulmonary vein ablation is hampered by safety concerns with a major complication rate around 6%, including stroke, pulmonary vein stenosis, cardiac tamponade, atrio-esophageal fistula and death. In most cases, complications of catheter ablation occur as a result of thermal injury to the atrium and surrounding structures. Limiting the amount of tissue targeted for ablation may prevent complications from thermal injury but may also compromise efficacy by leaving behind un-ablated sites that later serve as the substrate for recurrent AF. One of the major limitations of the anatomic approach to pulmonary vein ablation has been the inability to determine, in real-time, when enough tissue has been ablated to achieve a successful outcome—that is no recurrence of AF.

SUMMARY OF THE INVENTION

The present invention involves a method for recording a multiplicity of electrocardiographic signals in and/or on the heart and/or tissues and blood vessels that are connected to the heart and/or on the body surface, to determine susceptibility to atrial-rhythm disturbances.

In one embodiment, the present invention is a method for identifying a susceptibility of a subject to atrial-rhythm disturbances. The method includes a) placing a plurality of sensors on the subject to measure a physiologic signal of the subject, and b) recording the physiologic signal from the sensor. The physiologic signal includes an atrial electrical activity of the subject. The method includes c) determining a beat-to-beat variability in the atrial electrical activity of the subject. The beat-to-beat variability includes alternans of electrocardiographic waveforms of a predetermined number of a sequence of heart beats. The method includes d) determining a susceptibility to atrial-rhythm disturbances of the subject using the beat-to-beat variability in the atrial electrical activity determined in step c), and e) generating a report of the susceptibility to atrial-rhythm disturbances of the subject.

In another embodiment, the present invention is a method for identifying a susceptibility of a subject to atrial-rhythm disturbances. The method includes a) placing a sensor on the subject to measure a physiologic signal of the subject, and b) recording the physiologic signal from the sensor. The physiologic signal includes an electrical activity of a heart of the subject. The method includes c) determining a beat-to-beat variability in the atrial electrical activity of the subject during a sequence of heart beats, d) determining a susceptibility to atrial-rhythm disturbances of the subject using the beat-to-beat variability in the atrial electrical activity, and e) generating a report of the susceptibility to atrial-rhythm disturbances of the subject.

In another embodiment, the present invention is a system for identifying susceptibility to atrial-rhythm disturbances. The system includes a plurality of sensors configured to measure a physiologic signal of a subject, and a computer for recording the physiologic signal from the sensor. The physiologic signal includes an atrial electrical activity of the subject. The computer is configured to determine a beat-to-beat variability in the atrial electrical activity of the subject. The beat-to-beat variability includes alternans of electrocardiographic waveforms of a predetermined number of a sequence of heart beats. The computer is configured to use the beat-to-beat variability in the atrial electrical activity to determine a susceptibility to atrial-rhythm disturbances of the subject. The system includes a user interface for displaying the susceptibility to atrial-rhythm disturbances of the subject.

BRIEF DESCRIPTION OF THE DRAWINGS

For a more complete understanding of this disclosure, reference is now made to the following brief description, taken in connection with the accompanying drawings and detailed description, wherein like reference numerals represent like parts.

DETAILED DESCRIPTION

The present invention is directed to a system and method for assessing atrial electrical stability. More specifically, a system and method are provided for guiding radio-frequency catheter ablation to minimize instances of atrial fibrillation (AF). In one implementation, catheter ablation procedures are guided using measurements and analysis of atrial alternans, a beat-to-beat variation in the morphology of the atrial electrocardiographic (ECG) waveform. In some cases, atrial alternans are associated with the same myocardial substrate that gives rise to AF.

Electrical alternans are a pattern of variation in the shape of electrocardiographic waveform that appears on an every other beat basis. In humans, visible (macroscopic) alternations in ventricular repolarization have been associated with an increased vulnerability to ventricular arrhythmias under diverse pathophysiologic conditions.

A Fast Fourier Transform (FFT) spectral method may be used to detect microvolt level T-Wave Alternans (TWA) and the establishment of a relationship between TWA and Ventricular Fibrillation (VF) threshold (VFT). An increased dispersion of repolarization (DR) is an important condition for the development of reentrant arrhythmias and may be associated with both VT/VF and concordant or discordant alternans (DR is greater at sites of discordant vs. concordant alternans). In some cases, action potential (AP) duration (APD) alternans can provide the substrate for reentry, indicating that TWA is also a short-term predictor of arrhythmia susceptibility. Accordingly, the mechanisms that generate VRA (functional spatial dispersion of refractoriness) are likely to also lead to VT/VF, requiring that the heart pass through a VRA stage on the way to VT/VF or VRA occurs in conjunction with developing VT/VF.

Figure 1:
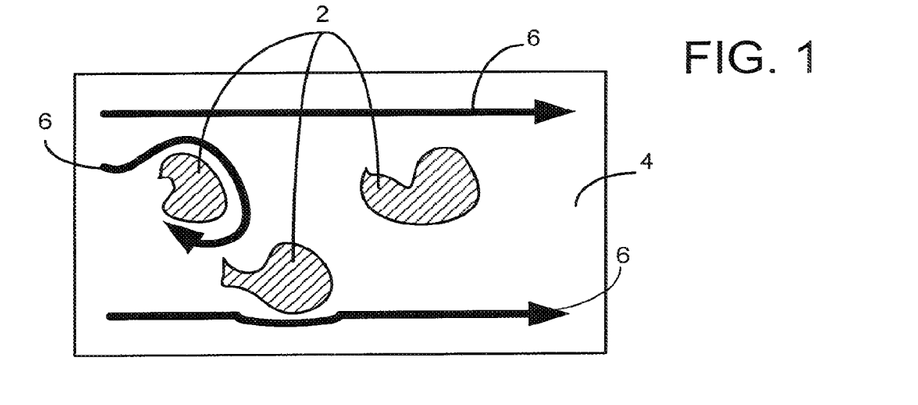
FIG. 1 is a schematic diagram illustrating the formation of spatial alternans in cardiac tissue leading to a dispersion of recovery, wave front fractionation, and reentry.

Action potential alternans involve an alternating sequence in which the shape of the action potential (the wave-like pattern of variation of a cell's transmembrane potential) associated with an individual cardiac cell changes on an every other beat basis. If the duration of the action potential alternates on an every other beat basis, then the duration of the refractory period also alternates in duration because the refractory period is generally comparable to the duration of the action potential. Thus, action potential alternans create a situation in which a region of the myocardium has a long refractory period on an every other beat basis. Referring to FIG. 1, on these alternate beats, regions 2 with long action potential duration alternans can create islands of refractory tissue with respect to areas 4 of short action potential duration alternans. These variations between the regions 2, 4 cause fractionation of activation wavefronts 6 and promote the development of reentry.

A major factor leading to the creation of ventricular arrhythmias during ischemia is dispersion of refractoriness. Dispersion of refractoriness is a measure of non-homogeneous recovery of excitability in a given mass of cardiac tissue (tissue is called refractory when it cannot be re-stimulated until it has recovered). In normal myocardium, the excitability is strictly proportional to the duration of repolarization. Reentry is the most likely mechanism of arrhythmia facilitated by enhanced dispersion of repolarization. The elements that are most often represented in the experimental or clinical models of arrhythmias attributed to reentry include non-uniform conduction, non-uniform excitability, and non-uniform refractoriness. An important mechanism for enhancing dispersion of the refractory period is alternation of the action potential from beat to beat.

Thus, as illustrated in FIG. 1, action potential alternans 2, 4, which generally occur in diseased tissue, can promote the formation of islands of refractory tissue which promote the development of reentry. Therefore, localized cardiac alternans may be reflected in the surface ECG as TWA. Concomitantly, localized regions of AP alternans that exhibit delayed recovery on an every other beat basis are intrinsically linked or even lead to increased repolarization gradients sufficient to produce unidirectional block and reentry. Therefore, localized AP alternans lead to TWA as well as to increased DR, wavefront fractionation, reentry and VT/VF.

Similarly to ventricular alternans, localized regions of atrial APD heterogeneity can be identified on the ECG waveform as atrial (depolarization and/or repolarization) alternans, and the presence of alternans of atrial electrocardiographic waveforms is linked to the gradients of repolarization that give rise to multiple-wavelets and AF. Furthermore, by identifying local regions and/or periods of heightened alternans of atrial electrocardiographic waveforms in the heart and/or tissues that are connected to the heart and targeting them, catheter ablation can sufficiently modify the electrical substrate to prevent AF. Suppression of alternans of atrial electrocardiographic waveforms may also be used as a marker for identifying a suitable end-point for ablation and limiting further thermal injury.

The use of alternans of atrial electrocardiographic waveforms to guide catheter ablation procedures of AF and verify and confirm its success, provides several advantages, such as: (i) a real-time, rapid and highly efficient method for identifying ablation targets based on electrophysiologic properties, not just anatomic markers; (ii) an approach that would limit thermal injury by preventing ablation of "non-culprit" atrial tissue; (iii) a marker to define the success of ablation and identify a procedural end point; (iv) a marker to predict long-term risk of arrhythmia recurrence; and (v) a broadly applicable approach to meet the substantial demand for AF therapy.

Heart rate variability (HRV), a variability of ventricular depolarization times, also acts as an indicator of sudden cardiac death in post myocardial infarction patients. As such, a mathematical model has been developed for describing HRV. In an analogous manner to measuring variability of ventricular depolarization times, the altered variability of atrial depolarization times and/or variability in the duration of atrial depolarization and/or variability in the duration from the onset of atrial depolarization to the offset of atrial repolarization and/or parameters of the signal averaged P-wave, may be intrinsically linked to periods of increased susceptibility of atrial arrhythmias and AF. Furthermore, identifying local regions and/or periods of altered variability of atrial depolarization times and/or variability in the duration of atrial depolarization and/or variability in the duration from the onset of atrial depolarization to the offset of atrial repolarization and/or parameters of the signal averaged P-wave and/or the tissues that it is connected, and targeting them for catheter ablation can sufficiently modify the electrical substrate to prevent AF.

As will be described, the present method involves recording electrocardiographic signals associated with the heart, tissues or blood vessels that are connected to the heart, and/or the body surface, to determine a susceptibility to atrial-rhythm disturbances. The atrial-rhythm disturbances may involve atrial tachycardia, atrial fibrillation, atrial flutter, or other disturbances to the operation of the atria. Using the present method, sites that originate atrial-rhythm disturbances are identified in the atria or tissues and blood vessels that are connected to the heart. After identifying the sites originating atrial-rhythm disturbances, appropriate medical treatments such as the delivery of a chemical or biochemical substance, or the application of electrical energy are guided to those sites. The present method may also involve determining the risk or likelihood of a subject to develop atrial-rhythm disturbances.

Figure 2:
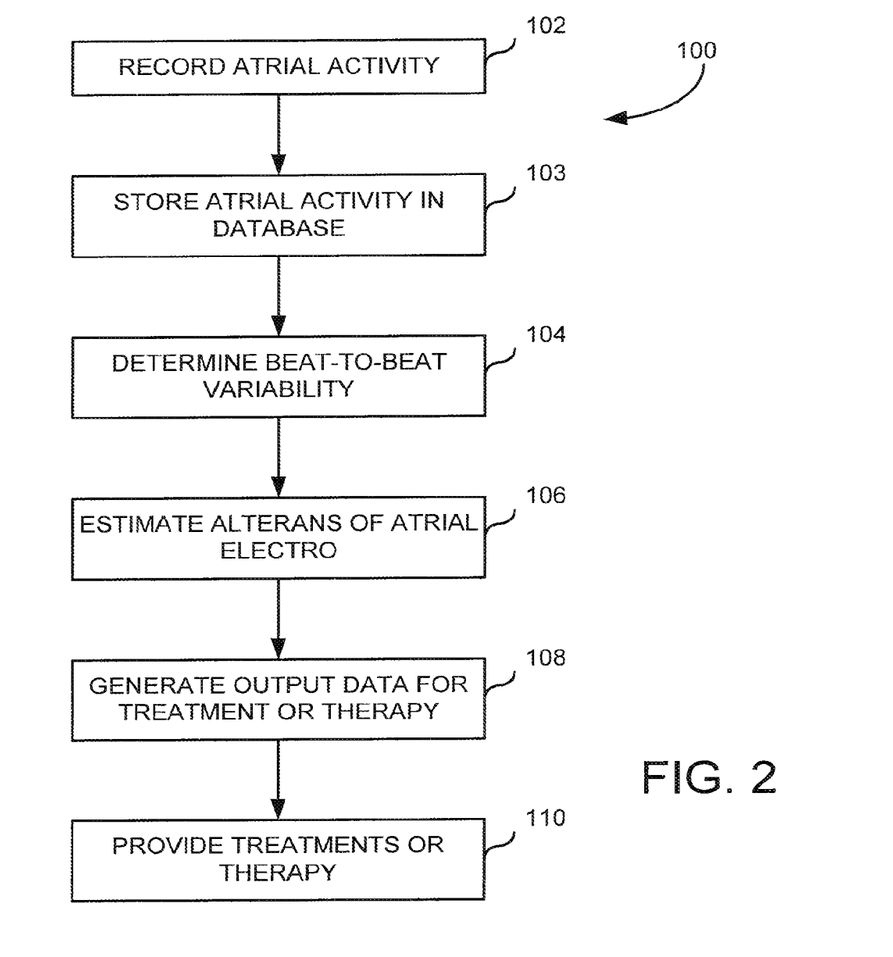
FIG. 2 is a flow chart setting forth the steps of a method for determining a subject's susceptibility to atrial-rhythm disturbances and for treating the subject to minimize the occurrences of atrial-rhythm disturbances.

FIG. 2 is a flow chart setting for the steps of an exemplary method 100 for determining a subject's susceptibility to atrial-rhythm disturbances and treating the subject to minimize the occurrences of atrial-rhythm disturbances. Using method 100, electrical activity originating in and/or on the heart and/or tissues and blood vessels that are connected to the heart and/or on the body surface are collected and processed. After processing, the system assesses a susceptibility to atrial-rhythm disturbances by further processing of atrial electrical activity data.

Figure 3:
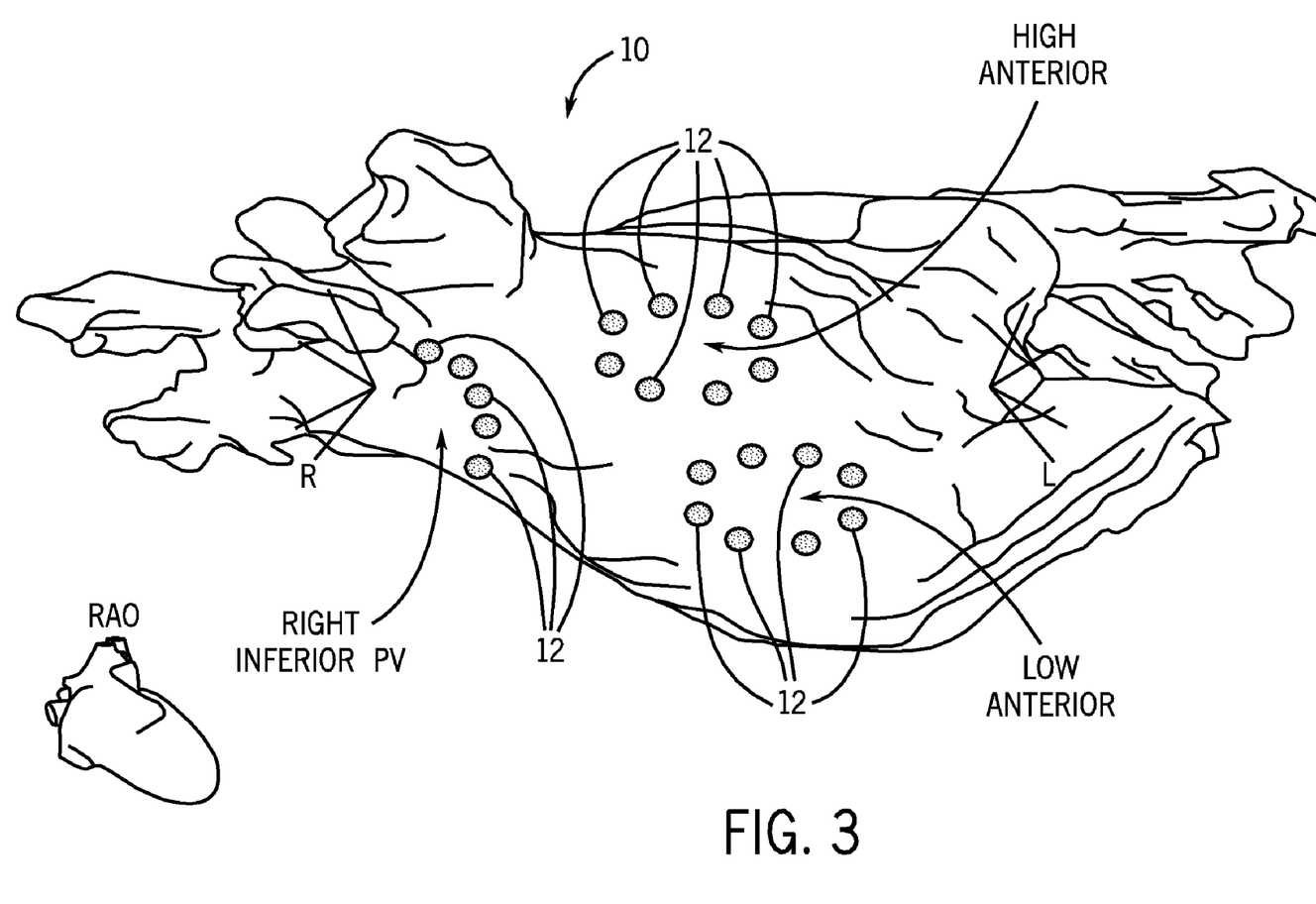
FIG. 3 is a three dimensional (3D) illustration of an anterior view of the left atrium and pulmonary veins of a heart indicating potential catheter lead locations.
Figure 4:
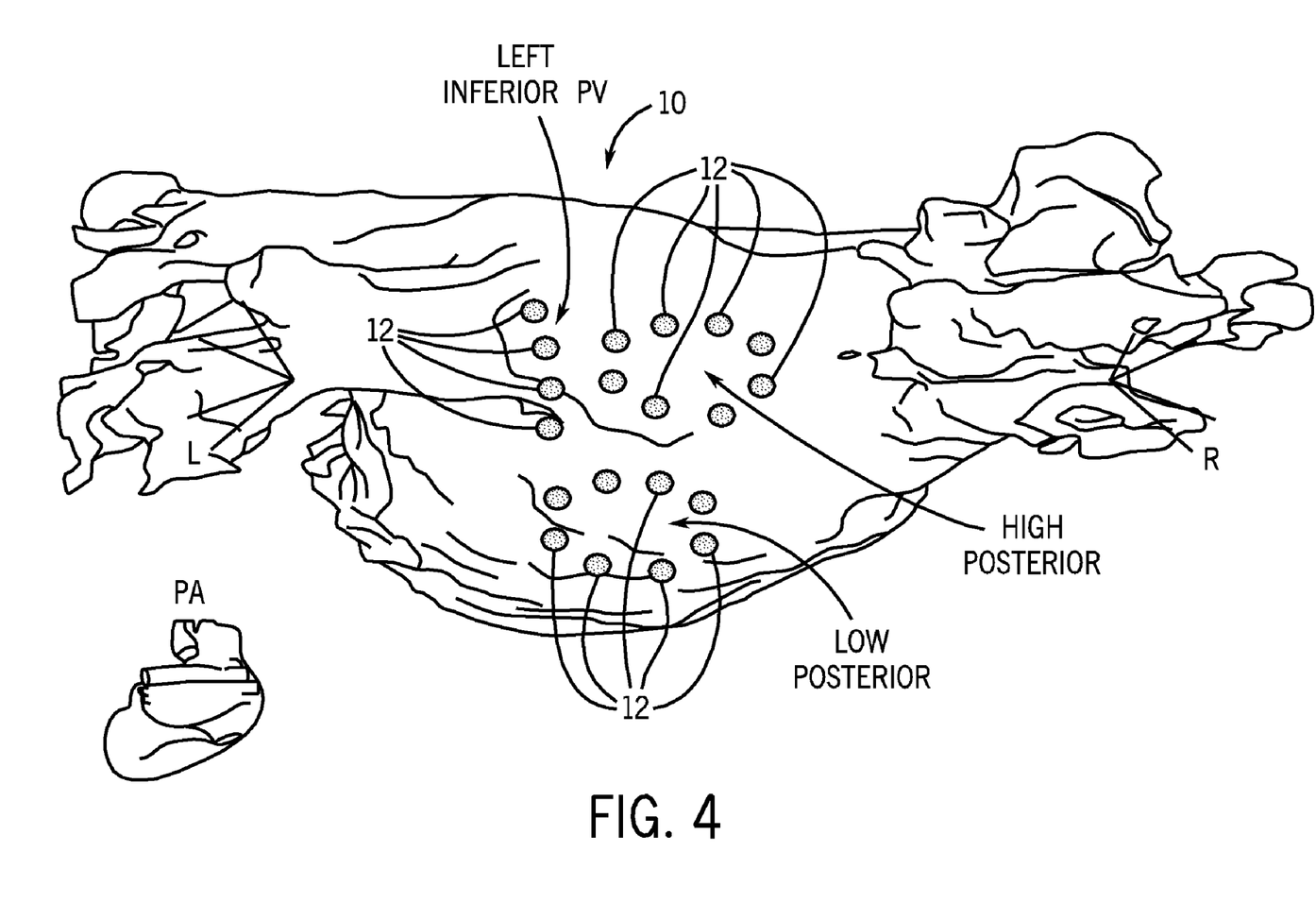
FIG. 4 is a 3D illustration of a posterior view of the left atrium and pulmonary veins of a heart indicating potential catheter lead locations.
Figure 5:
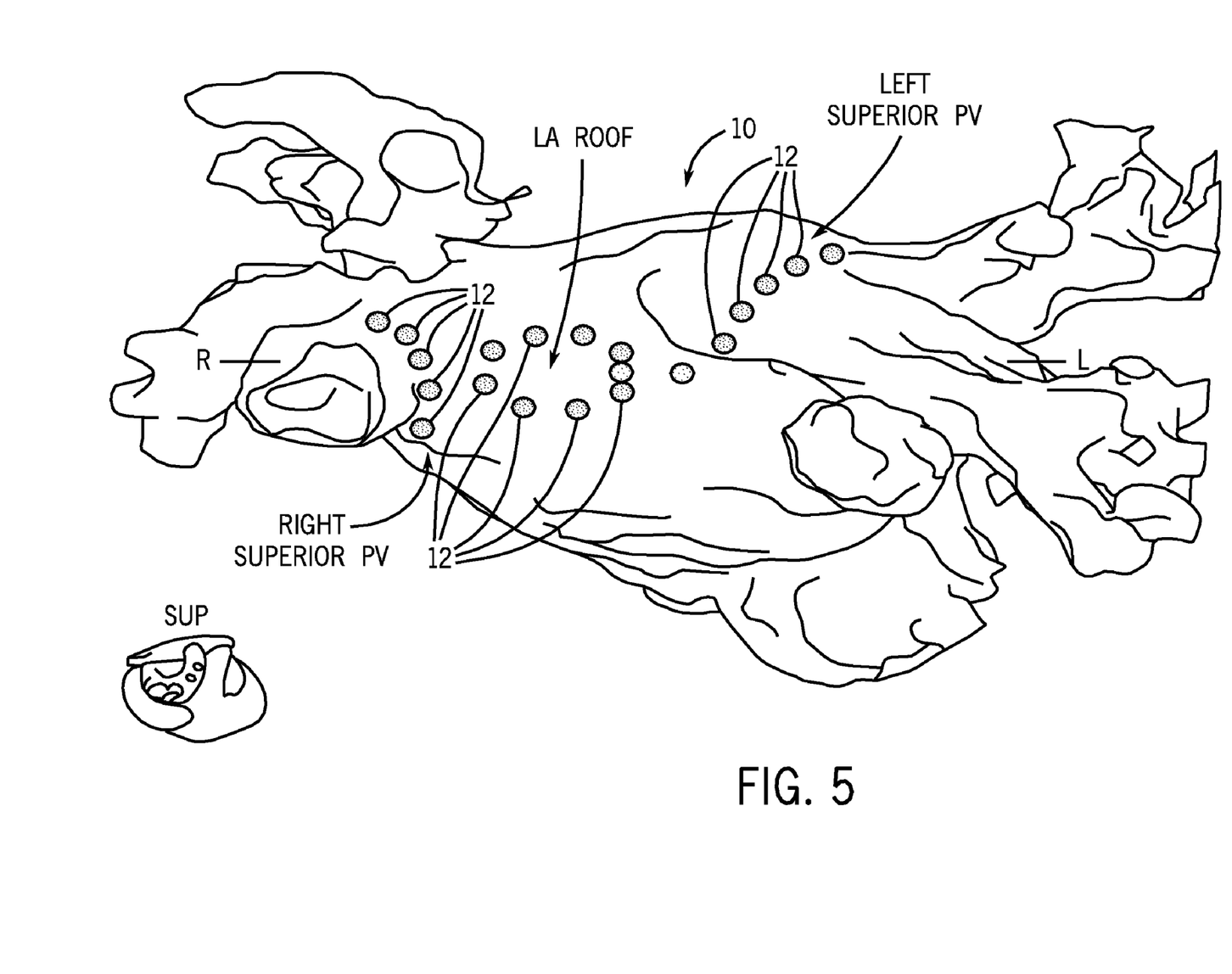
FIG. 5 is a 3D illustration of a top view of the left atrium and pulmonary veins of a heart indicating potential catheter lead locations.

In step 102, atrial activity of the heart is recorded using one or more electrodes connected to a subject to collect electrical data describing the activity of the heart tissue of the subject. The electrodes may include passive electrodes and may be placed in the atria, pulmonary veins, the coronary sinus, or any other tissue or blood vessels attached to the heart. FIGS. 3-5 illustrate a heart 10 of a subject having example placements of electrode or sensors 12 around a proximity of heart 10. FIG. 3 illustrates an anterior view of the left atrium and pulmonary veins of heart 10. FIG. 4 illustrates a posterior view of the left atrium and pulmonary veins of heart 10. FIG. 5 illustrates a top view of the left atrium and pulmonary veins of heart 10. In FIGS. 3-5, dots 12 indicate exemplary placement positions for the sensors or catheter leads.

The electrodes or sensors may be in a bipolar configuration for recording localized atrial electrical activity, or in a unipolar configuration for recording remote or global atrial electrical activity. Alternatively, atrial activity data may be collected using catheters similar to those used as part of the atrial fibrillation ablation procedure and the detected signals, following amplification, filtering and conditioning, are used for further analysis.

Depending upon system requirements, placement of the electrodes may optionally be guided or facilitated by the use of various imaging modalities, such as magnetic resonance imaging (MRI), computed tomography (CT) or ultrasound. The catheter lead location placement with respect to each other may be circular or straight. In one implementation, catheter leads in the heart (see, for example, FIGS. 3-5) may be positioned at or close to the pulmonary veins, in the high and/or low, anterior and/or posterior surfaces of the left atrium, or at any other tissue close to the atria, such as the coronary sinus. Catheter leads in the heart may be positioned at the corresponding sites in the right atrium and may occur sequentially at the aforementioned or different locations providing a detailed spatio-temporal (time-dependent anatomical) characterization of the beat-to-beat variability of atrial electrical activity.

In an alternative implementation, the leads for acquiring the electrocardiographic waveforms within or on the body may include Frank orthogonal leads or may be mathematically combined to form Frank orthogonal leads. In that case, the selected atrial waveforms of the three orthogonal bipolar leads (X, Y, Z) may be combined into a vector magnitude by the formula $(X^2+Y^2+Z^2)^{1/2}$.

Referring again to FIG. 2, step 102 may be implemented using leads of an implanted device such as an implantable cardioverter defibrillator or cardiac pacemaker. The devices may contain micro-processors or other electronic circuitry capable of performing the computations necessary for the measurement. Furthermore, the devices can also serve as a cardioverter defibrillator or pacemaker during the therapy portions of the present method.

At step 103, the signals representing the collected atrial activity data are stored in a computer or other electronic storage medium using an analog to digital card. In one implementation, the data is stored in a database, or other electronic storage medium on a computer's hard disk. After storage, the data is further processed to determine susceptibility to atrial-rhythm disturbances.

Figure 6:
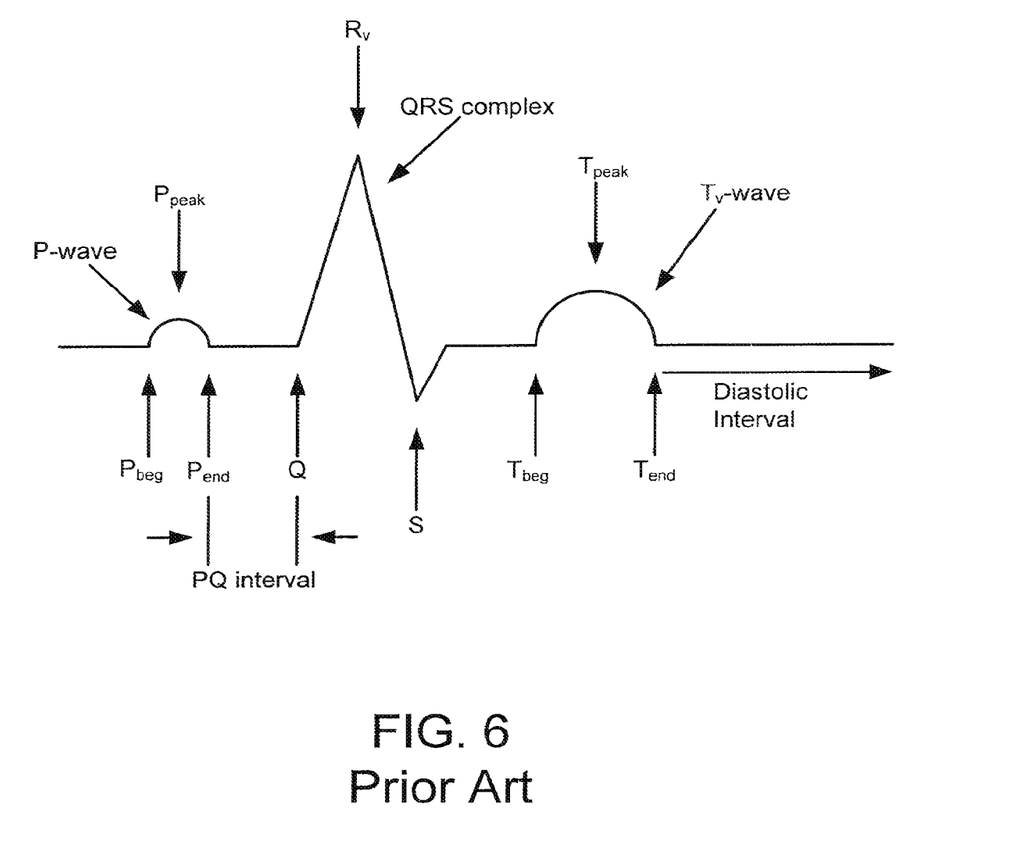
FIG. 6 is an exemplary electrocardiographic waveform including annotations identifying a plurality of portions of the electrocardiographic waveform.

In one implementation, the method continues by manipulating the data stored in step 103 to determine beat-to-beat variability in step 104. For example, the beat-to-beat variability may include atrial depolarization and/or repolarization alternans, or alternans of the PQ interval, as illustrated in FIG. 6. After determining beat-to-beat variability, the method includes estimating alternans of atrial electrocardiographic waveforms in step 106. Further detail of step 106 will be described with respect to FIG. 7.

After determining the alternans of atrial electrocardiographic waveforms, in step 108, output data is generated that may be used for treatment of the atrial-rhythm disturbances. For example, when the level of alternans of the selected atrial waveform estimated from one or more leads, exceeds a threshold value over some period of time (such as for example, one minute), susceptibility to atrial-rhythm disturbances may be indicated at step 108. Furthermore, when the level of alternans of the selected atrial waveform estimated from one lead, but not all leads, exceeds a threshold value over a predetermined period of time (such as for example, one minute), it may be determined that the site of origin of the atrial abnormal heart rhythm is close and/or around that lead, and susceptibility to atrial-rhythm disturbances may be indicated at that particular location. Successful elimination, interruption and/or isolation of the atrial heart-rhythm disturbances may be manifested by suppression and/or elimination of the alternans level of the selected atrial waveform. After detecting an on-going susceptibility to atrial-rhythm disturbances, various treatments or therapy are provided in step 110.

Figure 7:
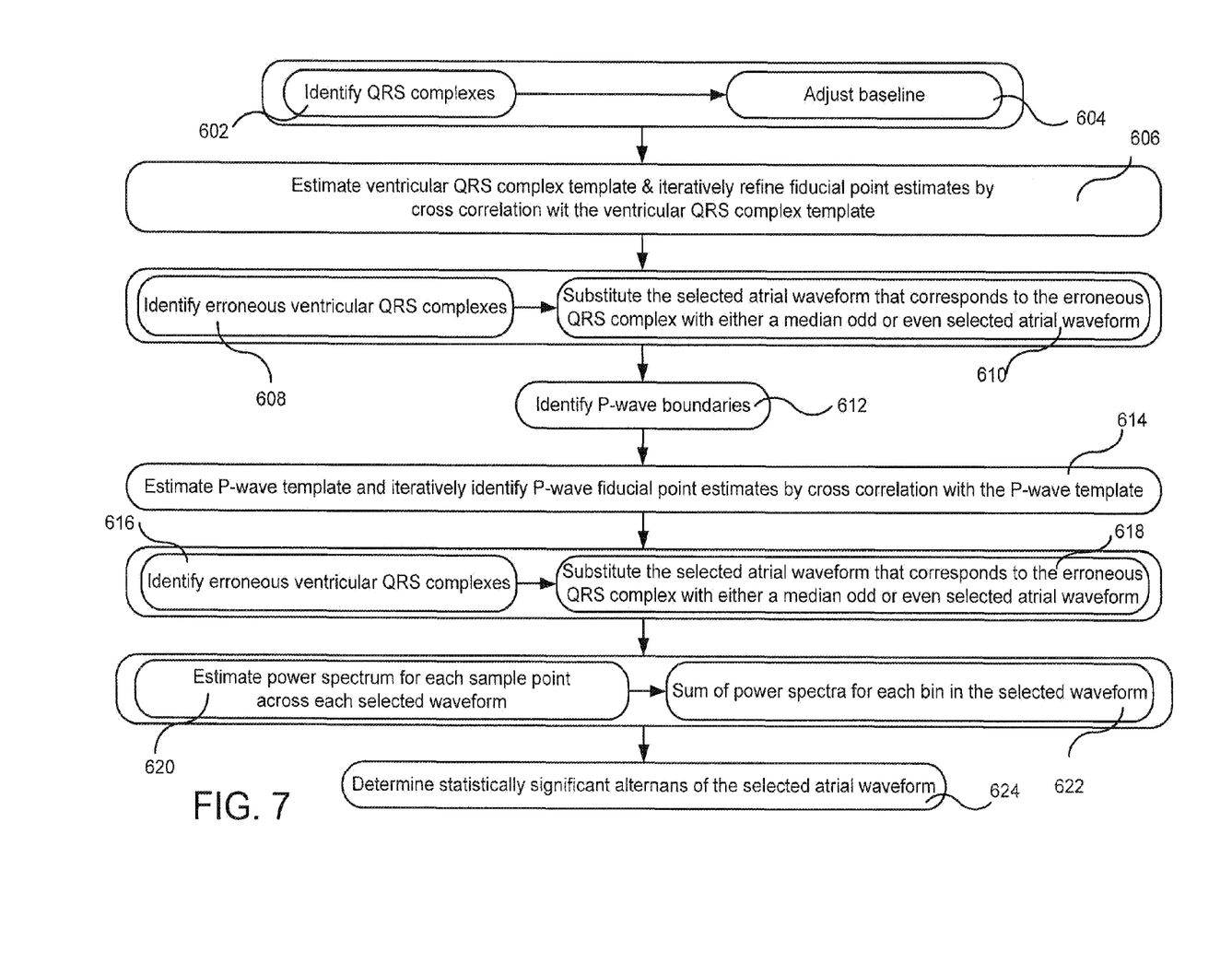
FIG. 7 is a flow chart illustrating the steps of an algorithm for estimating alternans of atrial electrocardiographic waveforms.

Referring now to FIG. 7, in one exemplary implementation, the process for estimating alternans of atrial electrocardiographic waveforms described with respect to step 106 of FIG. 2, may use 128 electrocardiographic waveforms and may be updated or shifted forward with every new electrocardiographic waveform recorded. The algorithm for estimating alternans of atrial electrocardiographic waveforms may be triggered either from the ventricular R-wave ($R_v$) of the QRS complex or the P-wave (seen in FIG. 6) in a double triggering approach in step 602. Double triggering first identifies the high amplitude ventricular $R_v$-wave and then a backwards algorithm may be applied to trigger on the P-wave. Alternatively, the algorithm for estimating alternans of atrial electrocardiographic waveforms may be triggered from the atrial $R_a$-wave.

The $R_v$-wave (indicating ventricular depolarization, as illustrated in FIG. 6) detection occurs in the electrocardiographic waveform obtained from any of the sensors placed in or on the patients' heart or tissues and blood vessels attached to the heart or on the patient's body surface. Following $R_v$-wave detection, the "baseline" for each beat (considered to be the mean or median value of the electrocardiographic waveform during the PQ interval seen in FIG. 6), may be adjusted by subtracting the baseline value from the value of the electrocardiographic waveform segment used for further analysis in step 604.

In another implementation, however, the PQ interval baseline can be adjusted by high-pass filtering. For example, to filter the effect of respiration at a rate of 9 breaths per minute on the ECG signal, a 128 order digital finite impulse response filter with a low cut-off frequency of 0.16 Hz with a normalized gain at that frequency at a magnitude of approximately −6 dB and having magnitude 1 at the pass-band may be used. Alternatively, the low cut-off frequency of the filter to reduce the effect of respiration on the ECG signal may be dynamically adjusted based on a real-time estimate of the respiration rate. In one implementation, for example, a high-pass filter impulse response is windowed with a 129 point length window (for example, Hamming or Hanning).

Following PQ interval baseline adjustment in step 604, an average or median ventricular QRS complex (for example, 70 milliseconds long) is formed and each ventricular QRS complex in the 128-beat sequence is repeatedly cross-correlated (convoluted) and shifted against the average or median ventricular QRS complex of that sequence of beats in step 606. The sample point at which the cross-correlation takes its maximum value is considered the true $R_v$-wave (fiducial point). To make the fiducial point as accurate as possible, an additional interpolation may optionally be performed to determine the fiducial point to the nearest sample point.

Following refinement in identifying the peak of the ventricular QRS complexes, erroneous ventricular QRS complexes are detected in step 608 based on at least one of two criteria: (i) the morphology criterion, in which the correlation coefficient between the present beat ventricular QRS complex and the average or median ventricular QRS complex of the, for example, 128-beat sequence, is less than a threshold value of, for example, 0.95; and (ii) the $R_v$-to-$R_v$ ($R_vR_v$) interval criterion, in which the present beat's $R_vR_v$ interval minus the mean $R_vR_v$ interval of the previous, for example, 5 beats is less/more than a threshold value of, for example, 50 milliseconds.

A beat may be classified as good if both the morphology (indicated as "1" in Table 1) and the $R_vR_v$-interval (indicated as "1" in Table 1) criteria are satisfied, as indicated in a decision matrix that may help classify beats. After the erroneous beats are detected, for each erroneous beat, the appropriate number of atrial electrocardiographic waveforms are removed from that sequence of beats, as indicated in Table 1 and step 610.

TABLE 1

Decision matrix for beat classification based on analysis of the ventricular QRS complex.

| Case | Morphology Criterion | $R_vR_v$ Criterion | Outcome | Removed Beats | Classification |
|---|---|---|---|---|---|
| 1 | 0 | 0 | 0 | 3 (previous + present + next) | Premature Ventricular Contraction |
| 2 | 0 | 1 | 0 | 2 (present + next) | Supraventricular |
| 3 | 1 | 0 | 0 | 2 (previous + present) | Aberrantly conducted sinus beat (i.e. bundle branch block) |
| 4 | 1 | 1 | 1 | 0 | Normal |

In one implementation, the fiducial point is shifted to the far left of the acquisition window enabling maximal visibility of the P-wave and the PQ interval. This allows for the identification of the P-wave boundaries ($P_{beg}$ and $P_{end}$) using either the raw ECG signal or its filtered version in step 612.

Following identification of the P-wave boundaries, an average or median P-wave may be estimated (for example, being 100 milliseconds long) and each P-wave in the 128-beat sequence is repeatedly cross-correlated (convoluted) and shifted against the average or median P-wave of that sequence of beats in step 614, and the sample point at which the cross-correlation takes its maximum value is considered the true P-wave peak (fiducial point). In some cases, to make the fiducial point increasingly accurate, an additional interpolation is performed to determine the fiducial point to the nearest sample point.

Following refinement in identifying the peak of the P-wave, erroneous P-waves may be detected based on one or more of the following criteria: (i) the morphology criterion (as it applies to the P-wave), in which the correlation coefficient between the present beat P-wave and the average or median P-wave of the beat sequence is less than a threshold value of, for example, 0.90, see step 616, and (ii) the P-to-P interval criterion in which the present beat's P-to-P interval minus the mean P-to-P interval of the previous, for example, 10 beats is less/more than a threshold value of, for example, 50 milliseconds.

A beat may be classified as good if the morphology indicated "1" in Table 2 criterion alone and/or the P-to-P interval indicated "1" in Table 2 criteria are satisfied, as indicated in a decision matrix that may help classify beats (Table 2). Again, once all of the erroneous beats are detected, then for each erroneous beat the appropriate number of the selected for analysis atrial electrocardiographic waveforms are removed from that sequence of beats, as indicated in Table 2.

TABLE 2

Decision matrix for beat classification based on analysis of the P-wave.

| Case | Morphology Criterion | $R_a R_a$ Criterion | Outcome | Removed Beats | Classification |
|------|----------------------|---------------------|---------|---------------|----------------|
| 1 | 0 | 0 | 0 | 3 (previous + present + next) | |
| 2 | 0 | 1 | 0 | 2 (present + next) | |
| 3 | 1 | 0 | 0 | 2 (previous + present) | |
| 4 | 1 | 1 | 1 | 0 | Normal |

Therefore, in a sequence of beats selected for analysis, after all erroneous beats are detected and for each erroneous beat the appropriate number of the selected atrial electrocardiographic waveforms are removed, the selected atrial electrocardiographic waveform of each removed beat is substituted with a median odd or even selected atrial electrocardiographic waveform template depending on whether the removed beat was an odd or an even one in that sequence in step 618. After the appropriate beat removal and substitution, a sequence of selected atrial electrocardiographic waveforms may be eligible for further analysis if the number of removed beats is, for example, less than 9%; if the latest condition is not satisfied, the sequence moves forward, is updated with, for example, a new beat, and steps 606 through 610 are repeated.

If an eligible sequence of beats is identified for further analysis, then for example, if the selected atrial electrocardiographic waveform is a P-wave, an average or median P-wave is obtained and the P-wave boundaries ($P_{beg}$ and $P_{end}$) are obtained as previously described. In another implementation an average or median $T_a$-wave (reflecting atrial repolarization) may also be obtained and its boundaries (beginning and end) are again obtained as previously described. The analysis that follows may be applied in either or all selected atrial waveforms reflecting or being part of atrial excitation (for example the P-wave reflecting atrial depolarization and the $T_a$-wave reflecting atrial repolarization).

In steps 620 and 622, the power spectrum may be estimated for each time-aligned sequence of sample points within the selected atrial waveform, as previously described. In one case, the selected atrial waveform is split into bins, each bin consisting of at least one sample point. The power spectra for each sample point in a bin may be averaged and the statistical estimates of alternans of atrial electrocardiographic waveforms (for example, the alternans voltage, noise and K-score) are obtained as previously described in step 624.

Estimation of alternans of atrial electrocardiographic waveforms can be performed on unipolar signals alone or in combination with bipolar signals in order to more accurately determine susceptibility to atrial-rhythm disturbances. In one example, the use of unipolar and/or bipolar signals may also determine more accurately the site of origin of the atrial-rhythm disturbance. For example, if alternans of atrial electrocardiographic waveforms are present in bipolar signals (e.g. obtained from a pulmonary vein) or unipolar signals (e.g. obtained from the coronary sinus) before treatment, then, if, after treatment of the atrial-rhythm disturbances, alternans of atrial electrocardiographic waveforms persist only in the unipolar signal, treatment at and/or around the site that the bipolar signal was recorded from may be determined to be successful, although there is at least one more site of origin of atrial-rhythm disturbances that should be treated.

In one example treatment system, the same catheters used to record the fluctuations in the beat-to-beat variability of the selected atrial waveform are used to deliver therapy to the heart via electrical stimulus, ablation, delivery of medication, or other treatment methods. One therapy method involves the delivery of electrical energy to the heart through electrodes in and/or on the heart. This electrical energy may suppress and/or terminate and/or isolate the initiation of atrial-rhythm disturbances at and/or around the site of origin of the abnormal atrial rhythm. The energy of this therapy would be appropriate to interrupt an atrial-rhythm disturbance, such as preventing AF from spreading to the atrial tissue. The therapy may include the delivery of a chemical or biochemical substance. The chemical substance may include a pharmacological agent or gene therapy that reduces the likelihood of an atrial-rhythm disturbance from occurring. The substance may be delivered into the blood stream or directly at and/or around the tissue site of origin of the atrial-rhythm disturbances.

Therapy may be delivered by an implanted device through electrodes in and/or on the heart and/or tissues and blood vessels that are connected to the heart. The device may be configured to implement the measuring and analysis methods illustrated in FIGS. 2 and 7 and described above. Accordingly, such an implanted device, in addition to performing the measuring steps described above (steps 100-102 of FIG. 2) may identify time periods and locations within the subject having an increased probability that a heart rhythm disturbance may occur and during which therapy may be delivered. For example the implantable device can incorporate means for generating electrical stimulating pulses of specified energies and apply the pulses to body tissue at specified times, and deliver the impulses used for pacing the heart at the appropriate times and energy levels. The electrical impulses may be delivered at varying inter-impulse intervals so as to increase the level of heart rate variability. For example, the inter-impulse intervals may have a mean of 600 milliseconds and a standard deviation of 120 milliseconds. In general, the mean inter-impulse interval is small enough so that most of the heart beats result from the applied impulses and not from spontaneous cardiac electrical activity. The variable inter-beat intervals will also cause the diastolic intervals associated with cardiac electrical activity in the heart's ventricles to vary. Since the STa and Ta-wave morphology also depend on the duration of the preceding diastolic interval, the variability in the timing of the electrical impulses will also cause increased variability in STa and Ta-wave morphology and thus tend to suppress ατριαλ repolarization alternans.

The delivered therapeutic electrical stimulus may have a minimum energy level similar to that delivered by pacemakers (pacing pulse), and a maximum energy level similar to that delivered by defibrillators (defibrillation shock). The therapeutic electrical stimulus should be delivered outside the vulnerable window wherein ventricular fibrillation may be induced. When there is alternation in the atrial beat duration (the duration of time from the beginning of depolarization to the end of repolarization), the electrical impulse is delivered at a time interval after the end of repolarization in the beats with the shorter beat duration. This time interval is longer than the diastolic interval that follows the beats with the longer beat duration but shorter than the diastolic interval that follows the beats with the shorter beat duration. Adaptive pacing can be employed in such a way that electrical stimuli will be applied on alternate beats during alternans.

In another implementation, non-excitatory current will be applied during the absolute refractory period to modulate the local atrial APD and, consequently, the QTa interval. Current pulses may be applied on a beat-to-beat basis during alternans by attempting to prolong (by applying a positive amplitude pulse or anodic stimulus) or shorten (by applying a negative amplitude pulse or cathodic stimulus) the QTa interval, on either the short (in an attempt to prolong it) or the long (in an attempt to shorten it) beats on alternate beats. In one implementation, the following parameters of the current pulses are adjusted to confirm suppression/termination of RA, the: (i) amplitude, (ii) duration, and (iii) delay from the Ra-wave. Monophasic square-wave current pulses with (i) peak amplitudes ranging between 1 and 20 mA in incremental steps of 1 mA (corresponding to an approximate range of 0.5 to 10V, for ~500 Ohms impedance), (ii) duration ranging from 10 to 50 milliseconds, in incremental steps of 2 milliseconds, and (iii) delivery of 10 to 50 milliseconds in incremental steps of 2 milliseconds after the Ra-wave, are applied on alternate beats.

Using the present method, the level of alternans of the selected atrial waveform may be quantified by obtaining the Fast Fourier Transform of the windowed auto-correlation function of a time-aligned sequence of sample points, and then obtaining a measurement of the alternans voltage, noise and the alternans ratio, in one or more electrocardiographic leads. Threshold values of these parameters can be established. For example, the threshold values may include 1.9 microvolts for the alternans voltage and a value of 3.0 for the alternans ratio. Other threshold values may require noise estimates during the alternans estimation to be below a value such as 1.8 microvolts.

Other threshold values may require that the optimal heart rate for the alternans estimation of the selected atrial waveform be, for example, 105 beats per minute or 5-40% above the patient's intrinsic heart rate. This threshold may be applied by pacing (electrical stimulation of the heart), exercise and/or delivery of a chemical (pharmacologic) substance. If pacing is used, the pacing pulse (artifact) may be eliminated by: (i) high-pass filtering of the ECG signal with a cut-off frequency of, for example, 180 Hz; (ii) application of a threshold algorithm on the filtered signal; or (iii) identification of the pacing pulses as the local maxima.

When determining estimates of the alternans voltage or the noise from the power spectrum, respiration may affect the amplitude of one or both of them. Accordingly, the respiration frequency may be monitored and the respiration affect on the amplitude of the power spectrum at the alternans frequency (for example, 0.5 cycles/beat) or the noise-band frequencies may be reduced or eliminated, by requiring the subject to breath at a different and specific breathing pattern, by appropriate filtering of the respiration signal, or by appropriately adjusting the estimation of the alternans voltage and noise, and the like.

Figure 8:
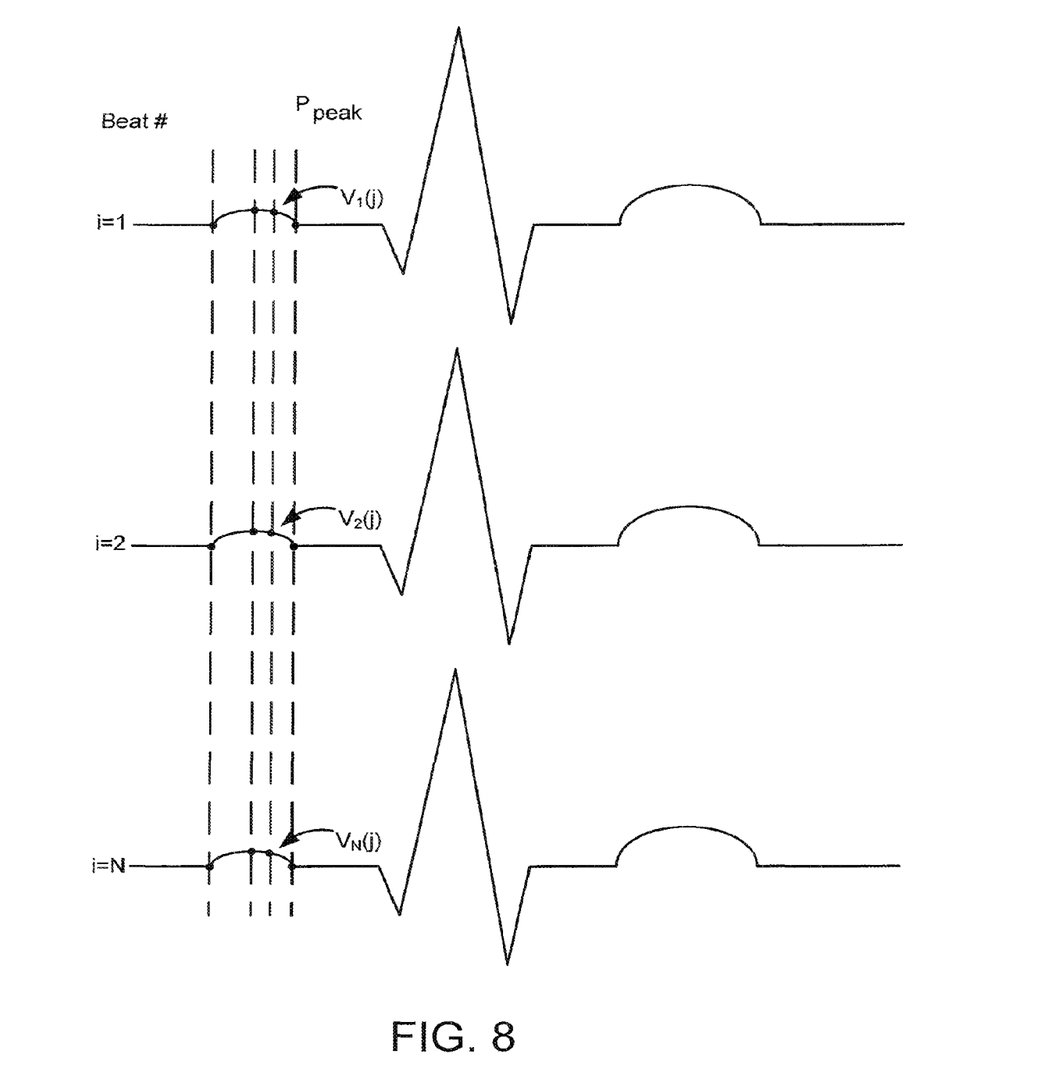
FIG. 8 shows a plurality of exemplary electrocardiographic waveforms illustrating time-aligned samples within the P-wave used for the depolarization alternans of atrial electrocardiographic waveforms estimation.

The beat-to-beat variability may be manifested as fluctuations of the selected atrial waveform at specific frequencies in the Fast Fourier Transform power spectrum; the amplitude of the Fast Fourier Transform power spectrum at such frequencies is higher ("dominant frequency") than other frequencies in the spectrum. The Fast Fourier Transform may be obtained on a sequence of time aligned points with respect to fiducial points of the selected atrial waveform (see, for example, FIG. 8), such as the peak of the P-wave or the peak of $T_a$-wave. Further analysis of these dominant frequencies may indicate the presence of a site of origin of atrial-rhythm disturbances, or the distance of the site of origin of the atrial-rhythm disturbances from the lead that recorded the specific electrocardiographic waveform. Identification of a dominant frequency may be also used to identify individuals susceptible to abnormal atrial rhythms over the long-term.

Alternatively, the beat-to-beat variability of the selected atrial electrocardiographic waveform may include a measurement of P-to-P interval variability. Reduced heart rate ($R_vR_v$) variability is a well known predictor of the development of ventricular arrhythmias. A threshold value of P-to-P interval variability may be established, such as the standard deviation of normal-to-normal (SDNN) P-to-P interval variability being, for example, equal to 60 milliseconds. When the P-to-P interval variability (estimated from atrial electrical activity recorded from a specific lead), is less than this threshold value for some period of time (for example one minute), then the site of origin of the atrial abnormal rhythm can be determined to be close and/or around that lead and therapy is delivered to eliminate and/or interrupt the atrial-rhythm disturbances. In that case, successful elimination and/or interruption of the atrial abnormal rhythm may be manifested by adjusting to normal the P-to-P interval variability.

Figure 9:
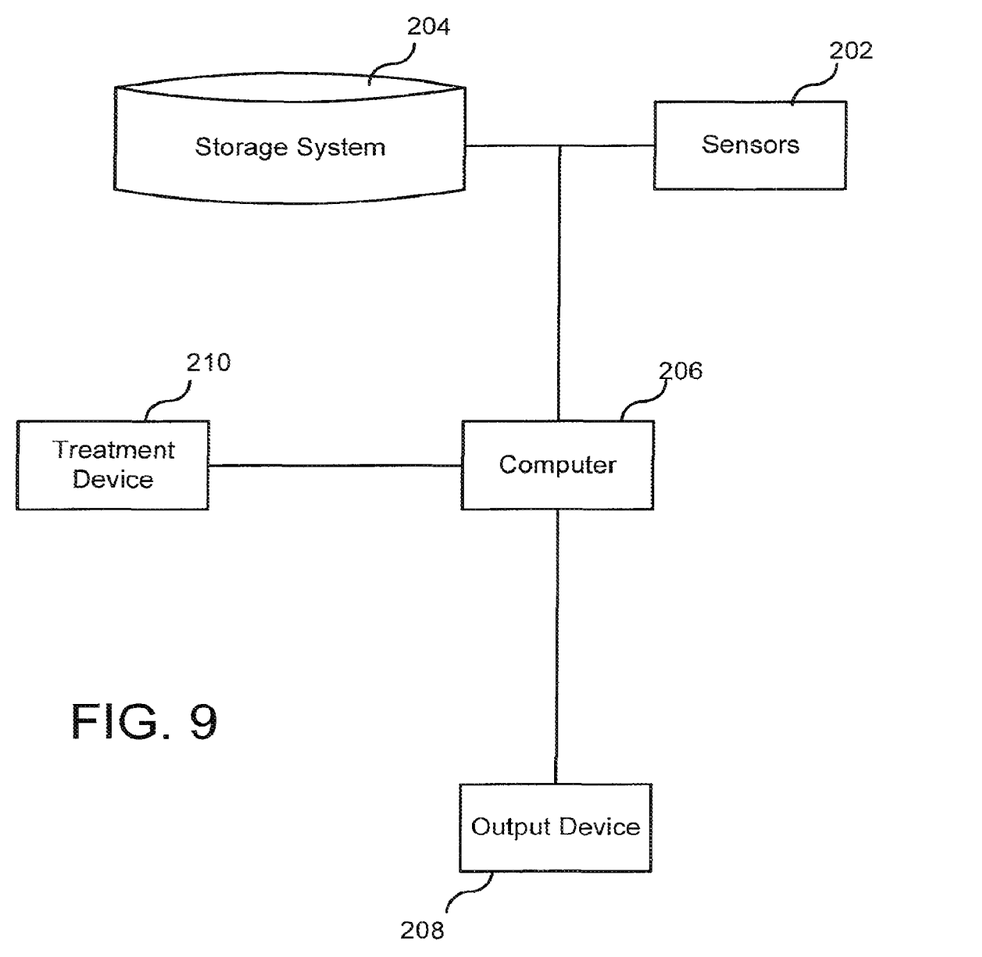
FIG. 9 is a schematic diagram of a system for assessing atrial electrical stability.

FIG. 9 illustrates a system 200 for assessing atrial electrical stability. System 200 includes one or more sensors 202 configured to detect atrial activity of the heart of a subject. Sensors 202 may include one or more electrodes and can be connected to a subject to collect electrical data describing the activity of the heart tissue of the subject. The electrodes may include passive electrodes and may be placed in the atria, pulmonary veins, the coronary sinus, or any other tissue or blood vessels attached to the heart. The electrodes may be in a bipolar configuration for recording localized atrial electrical activity, or in a unipolar configuration for recording remote or global atrial electrical activity. Alternatively, atrial activity data may be collected using catheters similar to those used as part of the atrial fibrillation ablation procedure and the detected signals, following amplification, filtering and conditioning, are used for further analysis.

Sensors 202 may include leads or electrodes of an implanted device such as an implantable cardioverter defibrillator or cardiac pacemaker. The devices may contain micro-processors or other electronic circuitry capable of performing the computations necessary for the measurement. Furthermore, the devices can also serve as a cardioverter defibrillator or pacemaker during the therapy portions of the present method.

In some implementations, sensors 202 are fabricated within a portable ambulatory electrocardiographic device that also continuously monitors the electrical activity of the heart for 24 hours or more (e.g., a Holter monitor). The extended recording period provided by the ambulatory electrocardiographic device may be used to capture and observe occasional cardiac arrhythmias that would be difficult to identify in a shorter period of time. For patients having more transient symptoms, a cardiac event monitor can be used. Unlike the Holter monitor, however, which records continuously throughout the testing period of 24 to 48 hours, the event monitor does not record until one feels symptoms and triggers the monitor to record ECG tracings at that time.

The Holter and the event monitor record electrical signals from the heart via a series of electrodes attached to the chest. The number and position of electrodes may vary, but most monitors employ from three to eight. These electrodes are connected to a small piece of equipment that is attached to the patient's belt, and is responsible for keeping a log of the heart's electrical activity throughout the recording period. On the other hand, the event monitor may wirelessly transmit the recording of the event to a physician or to a central monitoring center.

The electrical signals collected by sensors 202 represent atrial activity data are stored in a computer or other electronic storage medium 204. In one implementation, the data is stored in a database, or other electronic storage medium on a computer's hard disk. After storage, the data is further processed to determine susceptibility to atrial-rhythm disturbances.

The data stored in storage system 204 are retrieved by computer 206 for analysis. Computer 206 may include a personal computer, file server, workstation, minicomputer, mainframe, or any other computer capable of communicating and interconnecting with other computers. Input devices such as a mouse and/or a keyboard, a monitor, disk drives, memory, a modem, and a mass storage device such as a hard disk drive may be connected to computer 206. Computer 206 retrieves data from storage system 204 and is configured to implement one or more steps of the present method. For example, computer 206 may include software for retrieving data from storage system 204 and implemented the method illustrated in FIG. 2 or 7, for example.

Computer 206 is connected to output device 208 for outputting data generated by system 200. In one implementation, output device 208 includes a display system having a two-screen layout and/or a printer. One screen may display raw ECG signals as they are recorded from multiple sites (i.e. coronary sinus, pulmonary veins . . . ), while the second screen may display visual outputs for real-time estimates of atrial alternans magnitude.

System 200 includes treatment device 210 connected to computer 206 for administrating therapy to a subject. Treatment device 210 may include a mechanism for therapy may include the delivery of a chemical or biochemical substance. The chemical substance may include a pharmacological agent or gene therapy that reduces the likelihood of an atrial-rhythm disturbance from occurring. The substance may be delivered into the blood stream by treatment device 210 or directly at and/or around the tissue site of origin of the atrial-rhythm disturbances.

Alternatively, treatment device 210 includes an implanted device and is configured to generate electrical stimulating pulses of specified energies and apply the pulses to body tissue at specified times and deliver the impulses used for pacing the heart at the appropriate times and energy levels. The delivered therapeutic electrical stimulus may have a minimum energy level similar to that delivered by pacemakers (pacing pulse), and a maximum energy level similar to that delivered by defibrillators (defibrillation shock). The therapeutic electrical stimulus should be delivered outside the vulnerable window wherein ventricular fibrillation may be induced. When there is alternation in the atrial beat duration (the duration of time from the beginning of depolarization to the end of repolarization), the electrical impulse is delivered at a time interval after the end of repolarization in the beats with the shorter beat duration. This time interval is longer than the diastolic interval that follows the beats with the longer beat duration but shorter than the diastolic interval that follows the beats with the shorter beat duration. Adaptive pacing can be employed in such a way that electrical stimuli will be applied on alternate beats during alternans.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted, or not implemented.

Also, techniques, systems, subsystems and methods described and illustrated in the various embodiments as discrete or separate may be combined or integrated with other systems, modules, techniques, or methods without departing from the scope of the present disclosure. Other items shown or discussed as coupled or directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for identifying a susceptibility of a subject to atrial-rhythm disturbances, comprising the steps of:
    a) placing a plurality of sensors on the subject to measure a physiologic signal of the subject; b) recording the physiologic signal from the sensor, the physiologic signal including an atrial electrical activity of the subject; c) determining a beat-to-beat variability in the atrial electrical activity of the subject, the beat-to-beat variability including alternans of electrocardiographic waveforms of a predetermined number of a sequence of heart beats; d) determining a susceptibility to atrial-rhythm disturbances of the subject using the beat-to-beat variability in the atrial electrical activity determined in step c); and e) generating a report of the susceptibility to atrial-rhythm disturbances of the subject.

2. The method of claim 1, further comprising f) using the report of the susceptibility to determine a therapy plan including at least one of a delivery of a chemical substance and a delivery of electrical energy to the subject.

3. The method of claim 2, wherein the delivery of electrical energy includes delivering electrical energy during an absolute refractory period on alternate beats within the sequence of heart beats.

4. The method of claim 1, wherein step c) includes performing a Fast Fourier Transform to estimate alternans of the electrocardiographic waveforms.

5. The method of claim 1, wherein step c) includes identifying beat-to-beat variability created by at least one of atrial depolarization and repolarization alternans.

6. The method of claim 1, wherein step a) includes arranging the plurality of sensors in a bipolar configuration.

7. The method of claim 1, wherein step a) includes arranging the plurality of sensors in a unipolar configuration.

8. The method of claim 1, wherein step e) includes displaying the susceptibility to atrial-rhythm disturbances of the subject showing a first output showing raw electrocardiogram (ECG) signals of the subject and a second output showing the susceptibility to atrial-rhythm disturbances of the subject.

9. A method for identifying a susceptibility of a subject to atrial-rhythm disturbances, comprising the steps of:
a) placing a sensor on the subject to measure a physiologic signal of the subject; b) recording the physiologic signal from the sensor, the physiologic signal including an electrical activity of a heart of the subject; c) determining a beat-to-beat variability in the atrial electrical activity of the subject during a sequence of heart beats; d) determining a susceptibility to atrial-rhythm disturbances of the subject using the beat-to-beat variability in the atrial electrical activity; and e) generating a report of the susceptibility to atrial-rhythm disturbances of the subject.

10. The method of claim 9, further comprising f) determining a therapy location for a delivery of one of a chemical substance and an electrical energy to the subject to compensate for the susceptibility to atrial-rhythm disturbances of the subject.

11. The method of claim 10, wherein the delivery of electrical energy includes delivering electrical energy during an absolute refractory period on alternate beats in the sequence of heart beats.

12. The method of claim 9, wherein step c) includes performing a Fast Fourier Transform to estimate alternans of the electrocardiographic waveforms.

13. The method of claim 9, wherein the beat-to-beat variability is created by atrial depolarization or repolarization alternans.

14. The method of claim 9, wherein step e) includes displaying the susceptibility to atrial-rhythm disturbances of the subject via a user interface.

15. The method of claim 14, wherein displaying the susceptibility to atrial-rhythm disturbances of the subject via the user interface includes displaying a first output showing raw electrocardiogram (ECG) signals of the subject and a second output showing the susceptibility to atrial-rhythm disturbances of the subject.

16. A system for identifying susceptibility to atrial-rhythm disturbances, comprising:
a plurality of sensors configured to measure a physiologic signal of a subject; a computer for recording the physiologic signal from the sensor, the physiologic signal including an atrial electrical activity of the subject, the computer being configured to: determine a beat-to-beat variability in the atrial electrical activity of the subject, the beat-to-beat variability including alternans of electrocardiographic waveforms of a predetermined number of a sequence of heart beats, and
use the beat-to-beat variability in the atrial electrical activity to determine a susceptibility to atrial-rhythm disturbances of the subject; and a user interface for displaying the susceptibility to atrial-rhythm disturbances of the subject.

17. The system of claim 16, including a treatment device configured to deliver at least one of a chemical substance and electrical energy to the subject to compensate for the susceptibility to atrial-rhythm disturbances of the subject.

18. The system of claim 17, wherein the treatment device is configured to deliver electrical energy during an absolute refractory period on alternate beats in the sequence of heart beats.

19. The system of claim 16, wherein the plurality of sensors are configured to be arranged in a bipolar configuration.

20. The system of claim 16, wherein the plurality of sensors are configured to be arranged in a unipolar configuration.

21. The system of claim 16, wherein the user interface includes a first display configured to display raw electrocardiogram (ECG) signals of the subject and a second display configured to display the susceptibility to atrial-rhythm disturbances of the subject.

* * * * *